United States Patent
Kim

(10) Patent No.: US 9,622,707 B2
(45) Date of Patent: Apr. 18, 2017

(54) METHOD AND APPARATUS FOR PROCESSING SIGNAL

(71) Applicant: Samsung Electronics Co., Ltd., Suwon-si (KR)

(72) Inventor: Jong Pal Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 113 days.

(21) Appl. No.: 14/075,504

(22) Filed: Nov. 8, 2013

(65) Prior Publication Data

US 2014/0156197 A1 Jun. 5, 2014

(30) Foreign Application Priority Data

Dec. 4, 2012 (KR) ........................ 10-2012-0139347

(51) Int. Cl.
| | | |
|---|---|---|
| *G01N 33/48* | (2006.01) | |
| *G01N 33/50* | (2006.01) | |
| *A61B 5/00* | (2006.01) | |
| *G06F 19/12* | (2011.01) | |
| *G06F 19/26* | (2011.01) | |
| *G06F 19/28* | (2011.01) | |
| *A61B 5/04* | (2006.01) | |

(52) U.S. Cl.
CPC ........ *A61B 5/7207* (2013.01); *A61B 5/04012* (2013.01); *G06F 19/12* (2013.01); *G06F 19/26* (2013.01); *G06F 19/28* (2013.01)

(58) Field of Classification Search
None
See application file for complete search history.

(56) References Cited

U.S. PATENT DOCUMENTS

| 4,228,804 A | * | 10/1980 | Holasek et al. | ............ | 600/443 |
| 4,913,157 A | * | 4/1990 | Pratt et al. | ................... | 600/449 |
| 2007/0142735 A1 | | 6/2007 | Shin et al. | | |

FOREIGN PATENT DOCUMENTS

| KR | 1998-082617 A | 12/1998 |
| KR | 10-2006-0054644 A | 5/2006 |
| KR | 10-2006-0066708 A | 6/2006 |
| KR | 10-2006-0119472 A | 11/2006 |
| KR | 10-2007-0014251 A | 2/2007 |
| KR | 10-2007-0038310 A | 4/2007 |
| KR | 10-0721803 B1 | 5/2007 |
| KR | 10-2008-0017199 A | 2/2008 |

OTHER PUBLICATIONS

Clifton et al. Measurement of repiratory rate from the photop;ethysmogram in chest clinic patients. Journal of Clinical Monitoring and Computing, 2006, vol. 21, pp. 55-61.*

* cited by examiner

*Primary Examiner* — Russell S Negin
(74) *Attorney, Agent, or Firm* — NSIP Law

(57) ABSTRACT

A method of processing a signal may include receiving an input signal including a motion artifact, determining a filter parameter based on a frequency component of a motion-based signal analogous to the motion artifact, and filtering the input signal using a filter having the determined filter parameter.

16 Claims, 5 Drawing Sheets

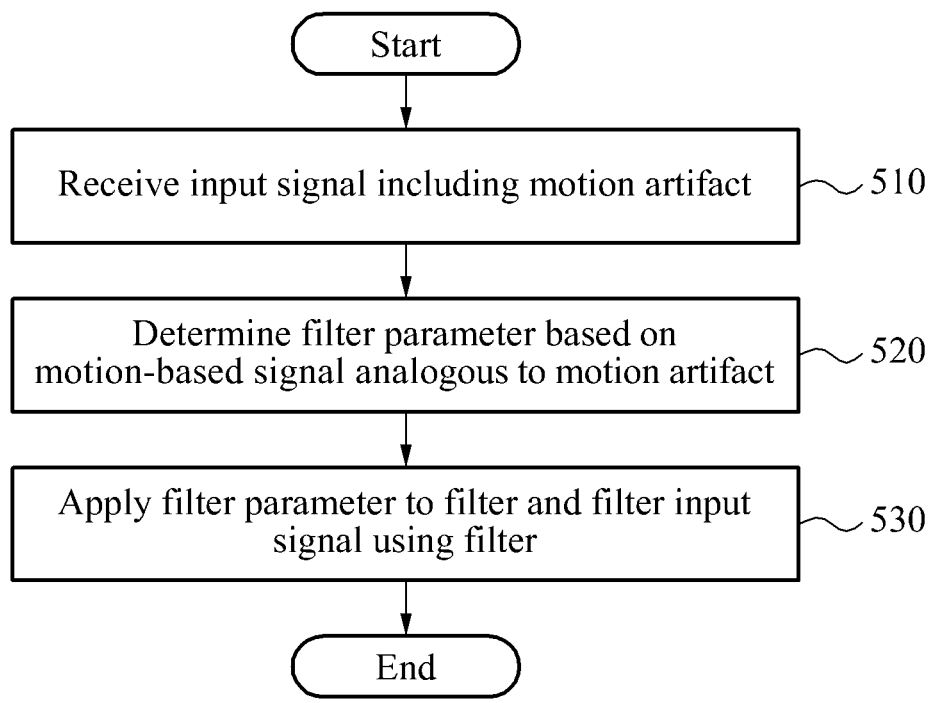

METHOD AND APPARATUS FOR PROCESSING SIGNAL

CROSS-REFERENCE TO RELATED APPLICATIONS

This application claims the benefit under 35 USC 119(a) of Korean Patent Application No. 10-2012-0139347 filed on Dec. 4, 2012, in the Korean Intellectual Property Office, the disclosure of which is incorporated herein by reference in its entirety for all purposes.

BACKGROUND

1. Field

This application relates to a method and apparatus for processing a signal including a motion artifact that may filter the signal by adjusting a filter parameter adaptively.

2. Description of Related Art

A biometric sensor used to measure a biometric signal, for example, an electrocardiography (ECG) sensor, an electromyography (EMG) sensor, a blood pressure sensor, and other biometric sensors, are being used widely. These sensors work in a dynamic environment, for example, a daily life of a user, as well as in a static environment, for example, a hospital room.

The ECG sensor measures an action potential generated during depolarization and repolarization of a heart muscle through a surface electrode attached to a human skin. However, when the ECG sensor is used in a dynamic environment, a motion artifact caused by the activity of the user may occur. As a result, the sensor may output an ECG signal including the motion artifact, resulting in an erroneous diagnosis.

To remove a motion artifact from an input signal, many solutions have been suggested. For example, a noise generation pattern may be recognized based on an activity pattern of a user, filter information may be selected for each section of a biometric signal based on the recognized noise generation pattern, and noise may be removed from the biometric signal based on the selected filter information. As another solution, an ECG signal and an EMG signal may be measured from a sensor, and the ECG signal may be filtered using the EMG signal as a reference signal.

However, despite these solutions, there is still a demand for an efficient and accurate technique for motion artifact removal.

SUMMARY

In one general aspect, a method of processing a signal may include receiving an input signal including a motion artifact; determining a filter parameter based on a frequency component of a motion-based signal analogous to the motion artifact; and filtering the input signal using a filter having the determined filter parameter.

The determining may include converting the motion-based signal to a frequency domain; identifying a frequency band having a highest power based on a power per frequency band in the motion-based signal converted to the frequency domain; and determining the filter parameter based on the identified frequency band.

The determining may further include selecting a filter parameter corresponding to the identified frequency band from predetermined filter parameters as the filter parameter.

The determining may include identifying a frequency band having a highest mean value or a highest integral value based on a mean value or an integral value per frequency band in the motion-based signal using a filter bank; and determining the filter parameter based on the identified frequency band.

The determining may further include selecting a filter parameter corresponding to the identified frequency band from predetermined filter parameters as the filter parameter.

The determining may include determining the filter parameter based on a relative frequency band difference between frequency components of the input signal and the motion-based signal.

The determining may include determining the filter parameter using a function relation between the frequency component of the motion-based signal and the filter parameter.

The determining may include determining either one or both of an order of the filter and a coefficient of the filter based on the frequency component of the motion-based signal.

The filtering may include filtering the input signal adaptively using the motion-based signal and the filter.

In another general aspect, a method of processing a signal may include determining a filter parameter based on a frequency component of an input signal and a frequency component of a motion-based signal; applying the determined filter parameter to a filter; and removing a motion artifact from the input signal using the filter; wherein the motion-based signal is similar to the motion artifact.

In another general aspect, a apparatus for processing a signal may include an input signal receiving unit configured to receive an input signal including a motion artifact; a parameter determining unit configured to determine a filter parameter based on a frequency component of a motion-based signal analogous to the motion artifact; and an input signal filtering unit configured to filter the input signal using a filter having the determined filter parameter.

The parameter determining unit may be further configured to convert the motion-based signal to a frequency domain; identify a frequency band having a highest power based on a power per frequency band in the motion-based signal converted to the frequency domain; and determine a filter parameter based on the identified frequency band.

The parameter determining unit may be further configured to select a filter parameter corresponding to the identified frequency band from predetermined filter parameters as the filter parameter.

The parameter determining unit may be further configured to identify a frequency band having a highest mean value or a highest integral value based on a mean value or an integral value per frequency band in the motion-based signal using a filter bank; and determine the filter parameter based on the identified frequency band.

The parameter determining unit may be further configured to select a filter parameter corresponding to the identified frequency band from predetermined filter parameters as the filter parameter.

The parameter determining unit may be further configured to determine the filter parameter based on a relative frequency band difference between frequency components of the input signal and the motion-based signal.

The parameter determining unit may be further configured to determine the filter parameter using a function relation between the frequency component of the motion-based signal and the filter parameter.

The parameter determining unit may be further configured to determine either one or both of an order of the filter and a coefficient of the filter based on the frequency component of the motion-based signal.

The input signal filtering unit may be further configured to filter the input signal adaptively using the motion-based signal and the filter.

The apparatus may further include a motion-based signal receiving unit configured to receive the motion-based signal analogous to the motion artifact.

Other features and aspects will be apparent from the following detailed description, the drawings, and the claims.

BRIEF DESCRIPTION OF THE DRAWINGS

FIG. 5 is a flowchart illustrating an example of a signal processing method.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein and may be changed as will be apparent to one of ordinary skill in the art, with the exception of operations necessarily occurring in a certain order. Also, description of functions and constructions that are well known to one of ordinary skill in the art may be omitted for increased clarity and conciseness.

Figure 1:
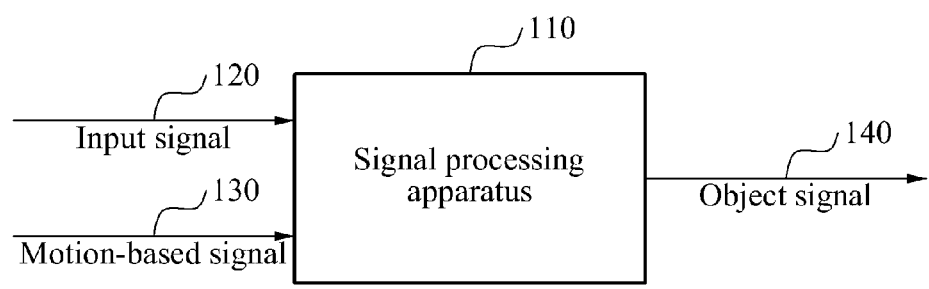
FIG. 1 is a diagram illustrating an example of an entire operation of a signal processing apparatus.

FIG. 1 is a diagram illustrating an example of an entire operation of a signal processing apparatus 110. When a biometric signal, for example, an electrocardiography (ECG) signal, is measured through a sensor in a dynamic environment, for example, in an active environment of a user, a motion artifact caused by the activity of the user may occur in an output signal. The motion artifact may cause distortion of the biometric signal, resulting in erroneous interpretation of the biometric signal.

The motion artifact may correspond to noise caused by a movement of the user or the sensor or a relative difference in displacement between a skin of the user and the sensor. When the user moves, a movement distance of the user skin and a movement distance of the sensor may differ, leading to the relative difference in displacement. The motion artifact may be measured through an electrode of the sensor by, for example, a half cell potential (HCP) or an impedance.

Referring to FIG. 1, the signal processing apparatus 110 measures an input signal 120, and measures a motion-based signal 130 analogous to a motion artifact to be used in removing the motion artifact from the input signal 120. The signal processing apparatus 110 filters the input signal 120 using the motion-based signal 130. The signal processing apparatus 110 may determine a filter parameter adaptively based on a frequency component of the motion-based signal 130, and may perform optimum filtering for characteristics of the motion artifact and the input signal 120.

After the signal processing apparatus 110 filters the input signal 120, the signal processing apparatus 110 may output an object signal 140 desired by a user to be measured or output. The object signal 140 is a signal obtained by removing the motion artifact from the input signal 120. The signal processing apparatus 110 may remove the motion artifact from the input signal 120 based on the frequency component of the motion-based signal 130. The signal processing apparatus 110 may remove the motion artifact from the input signal 120 efficiently using the motion-based signal 130 having a similar frequency characteristic to that of the motion artifact.

FIGS. 2A through 2D are diagrams illustrating an example of determining an optimum filter.

In FIGS. 2A through 3D, the signal processing apparatus may use a least mean squares (LMS) algorithm-based adaptive filter, hereinafter referred to as an LMS adaptive filter. The LMS adaptive filter may have a filter order N and an adaptive constant "mu as input parameters.

Figure 2A:
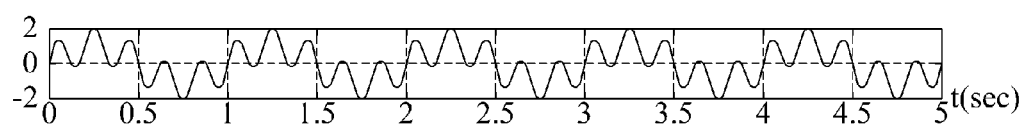
FIGS. 2A through 2D are diagrams illustrating an example of determining an optimum filter parameter.
Figure 2B:
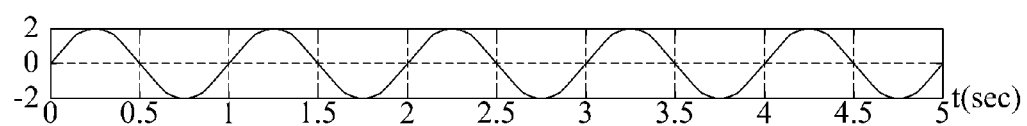
Figure 2C:
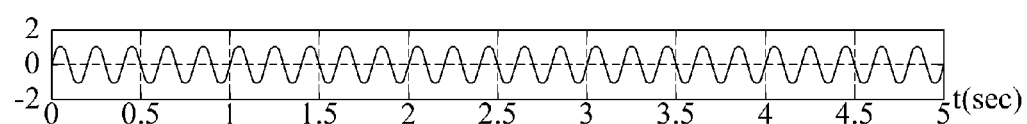

FIG. 2A illustrates an example of a simulation waveform of an object signal of a 5 hertz (Hz) sine wave combined with an input signal including a motion artifact of a 1 Hz sine wave. FIG. 2B illustrates a simulation waveform of a motion-based signal analogous to the motion artifact of the 1 Hz sine wave. FIG. 2C illustrates a simulation waveform of the object signal of the 5 Hz sine wave.

Figure 2D:
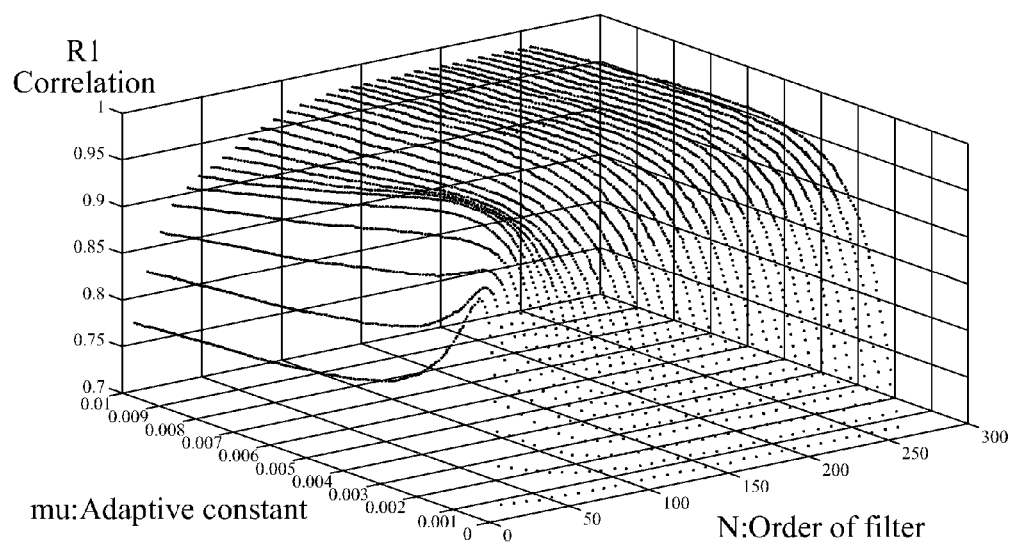

The filter order N and the adaptive constant "mu" of the LMS adaptive filter may be adjusted so that a correlation R1 between the input signal and the object signal is a maximum. FIG. 2D illustrates a simulation result in which R1=0.9967 when N=256 and mu=0.0045. The simulation result shows that correlation R1 changes with a filter order N and the adaptive constant "mu".

Figure 3A:
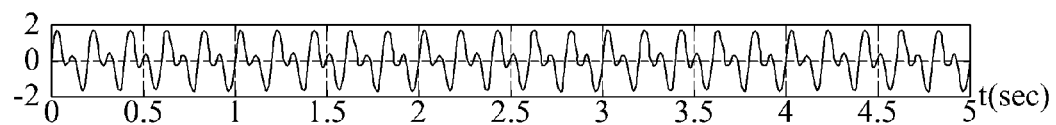
FIGS. 3A through 3D are diagrams illustrating another example of determining an optimum filter parameter.
Figure 3B:
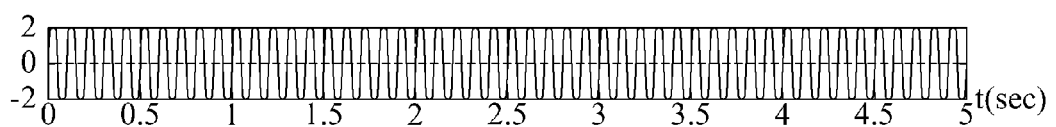
Figure 3C:
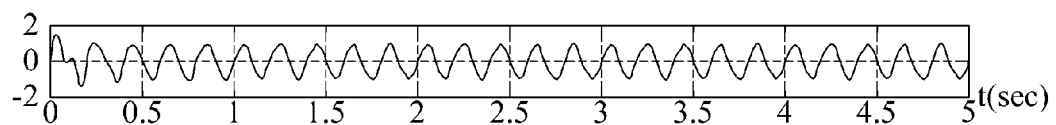
Figure 3D:
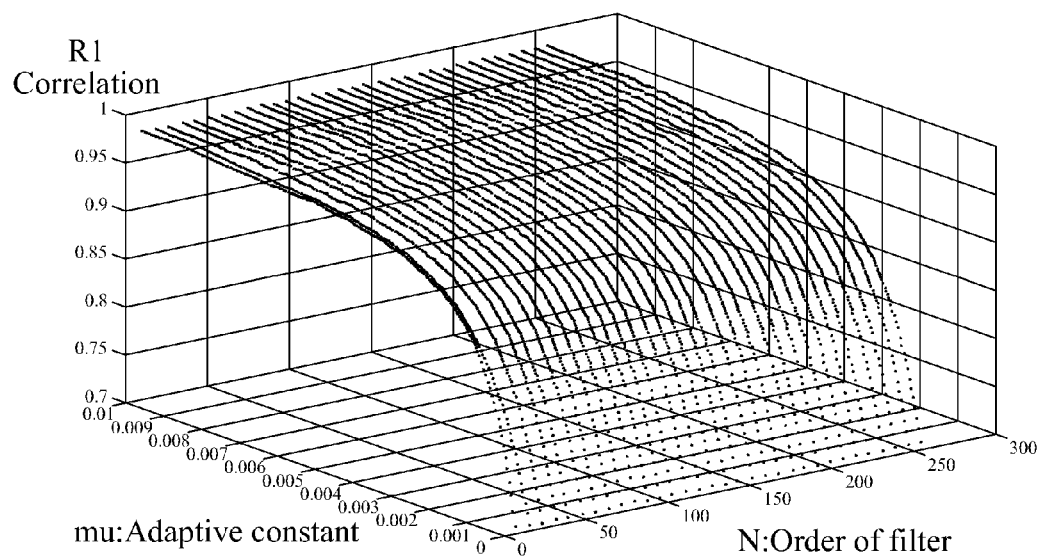

FIGS. 3A through 3D are diagrams illustrating another example of determining an optimum filter parameter. FIG. 3A illustrates a simulation waveform of an object signal of a 5 Hz sine wave combined with an input signal including a motion artifact of a 10 Hz sine wave. FIG. 3B illustrates a simulation waveform of a motion-based signal analogous to the motion artifact of the 10 Hz sine wave. FIG. 3C illustrates a simulation waveform of the object signal of 5 Hz sine wave.

The motion-based signal of FIG. 3 has a frequency ten times higher than that of FIG. 2, and has a higher frequency than the object signal. FIG. 3D illustrates a simulation result in which R1=0.9866 when N=2 and mu=0.01.

Based on the results of FIGS. 2A through 3D, it can be seen that an optimum filter parameter may change with a frequency characteristic of a motion-based signal. The optimum filter parameter may be stored in the signal processing apparatus based on the frequency characteristic of the motion-based signal.

The optimum filter parameter may be stored, for example, in a table, and the signal processing apparatus may determine a filter parameter to be applied to a filter by identifying the filter parameter mapped to the frequency component of the motion-based signal. The signal processing apparatus may filter the input signal based on the determined parameter.

Figure 4:
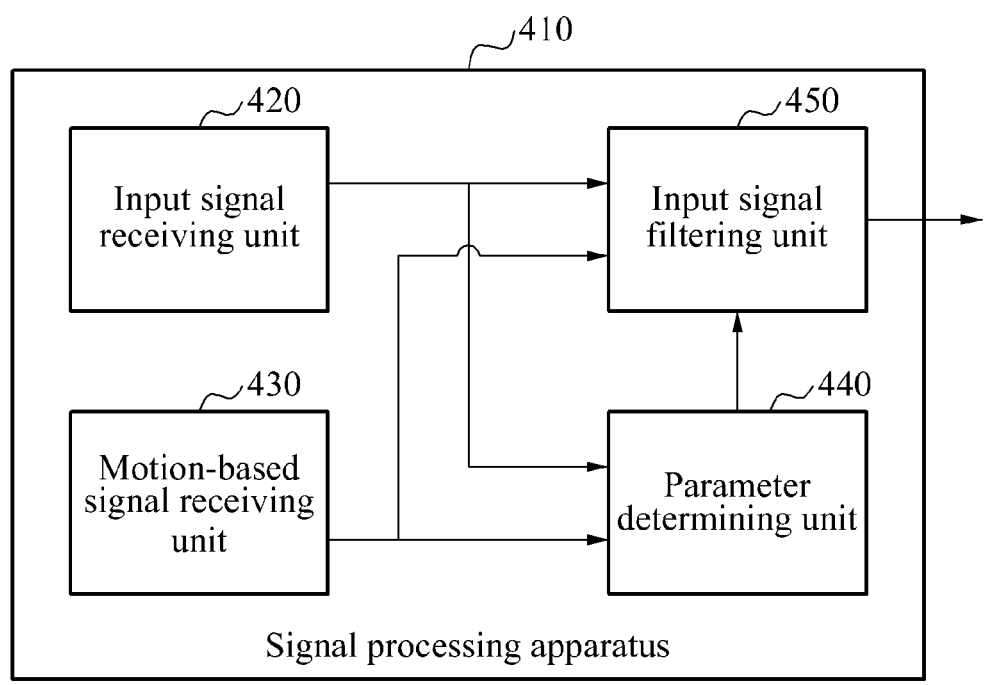
FIG. 4 is a block diagram illustrating an example of a structure of a signal processing apparatus.

FIG. 4 is a block diagram illustrating an example of a structure of a signal processing apparatus 410. Referring to FIG. 4, the signal processing apparatus 410 may include an input signal receiving unit 420, a motion-based signal receiving unit 430, a parameter determining unit 440, and an input signal filtering unit 450.

The input signal receiving unit 420 may receive an input signal including a motion artifact. The input signal receiving unit 420 may include, for example, a sensor attached to a body of a user to measure a biometric signal. The input signal received by the input signal receiving unit 420 is transmitted to the parameter determining unit 440 and to be used to determine a filter parameter.

The motion-based signal receiving unit 430 may receive a motion-based signal analogous to a motion artifact included in the input signal. For example, the motion-based signal receiving unit 430 may include a sensor, for example, an HCP sensor, an impedance sensor, an acceleration sensor, and any other sensor known to one of ordinary skill in the art capable of measuring a motion-based signal. The HCP sensor may measure a potential difference between a skin of the user and an electrode of the sensor. The impedance sensor may be disposed to be in contact with the skin of the user to measure a bioimpedance. The HCP sensor and the impedance sensor may output, as a potential change and an impedance change, respectively, noise caused by the movement of the user or the sensor.

The motion-based signal received by the motion-based signal receiving unit 430 may be transmitted to the parameter determining unit 440, and may be used to determine a filter parameter. Also, the motion-based signal may be transmitted to the input signal filtering unit 450, and may be used to filter the input signal.

The parameter determining unit 440 may determine a filter parameter for filtering the input signal based on a signal characteristic of the motion-based signal analogous to the motion artifact. The parameter determining unit 440 may determine the filter parameter based on a frequency component of the motion-based signal. For example, the parameter determining unit 440 may determine either one or both of a filter order and a filter coefficient based on the frequency component of the motion-based signal. The filter coefficient may include an adaptive constant of a filter.

The parameter determining unit 440 may convert the motion-based signal to a frequency domain, may identify a frequency band having a highest power based on a power per frequency band in the motion-based signal converted to the frequency domain, and may determine a filter parameter based on the identified frequency band. For example, the parameter determining unit 440 may identify the frequency band having the highest power based on the power per frequency band in the motion-based signal by performing a fast Fourier transform (FFT) on the motion-based signal.

The parameter determining unit 440 may select a filter parameter corresponding to the identified frequency band from predetermined filter parameters. For example, the parameter determining unit 440 may set a center frequency of the identified frequency band to be a reference value for determining a filter parameter, and may select a filter parameter corresponding to the reference value.

The parameter determining unit 440 may identify a frequency having a greatest magnitude by performing a FFT on the motion-based signal. The parameter determining unit 440 may set the frequency having the greatest magnitude to be a reference value for determining a filter parameter, and may select a filter parameter corresponding to the reference value.

The filter parameters corresponding to each reference value may be determined in advance, and may be stored, for example, in a lookup table. For example, the parameter determining unit 440 may identify a filter order or a filter coefficient corresponding to the reference value in the lookup table, and may provide the identified parameter to the input signal filtering unit 450.

The parameter determining unit 440 may determine a filter parameter using a filter bank. For example, the parameter determining unit 440 may identify a frequency band having a highest mean value or a highest integral value based on a mean value or an integral value per frequency band in the motion-based signal, and may determine a filter parameter based on the identified frequency band. The parameter determining unit 440 may use the filter bank rather than performing an FFT when determining the filter parameter to reduce the system resources required to determine the filter parameter.

The parameter determining unit 440 may use the input signal in addition to the motion-based signal to determine the filter parameter. The parameter determining unit 440 may determine the filter parameter based on a relative frequency band difference between the frequency component of the input signal and the frequency component of the motion-based signal.

For example, the parameter determining unit 440 may set a first reference value based on the frequency component of the input signal. The parameter determining unit 440 may convert the motion-based signal to a frequency domain, may identify a frequency band having a highest power based on a power per frequency band in the input signal converted to the frequency domain, and may set a center frequency of the identified frequency band to be a first reference value. The parameter determining unit 440 may identify a frequency band having a highest mean value or a highest integral value based on a mean value or an integral value per frequency band using a filter bank, and may set a center frequency of the identified frequency band to be a first reference value.

The parameter determining unit 440 may set a second reference value by performing the same method on the motion-based signal. The parameter determining unit 440 may determine whether the frequency band of the motion-based signal is higher or lower than the frequency band of the input signal by comparing the first reference value of the input signal with the second reference value of the motion-based signal. The parameter determining unit 440 may determine different parameters based on the determined result.

In other examples, the parameter determining unit 440 may identify a type of the input signal by analyzing the frequency component of the input signal. For example, the parameter determining unit 440 may determine whether the input signal is an ECG signal or an EMG signal by analyzing the frequency characteristic of the input signal. Since ECG signals or EMG signals of different users have similar frequency characteristics, the parameter determining unit 440 may identify the type of the input signal based on the frequency characteristic of the input signal. When the type of the input signal is identified, the parameter determining unit 440 may determine a parameter table corresponding to the identified type of the input signal. The parameter table corresponding to each type of the input signal may include a parameter corresponding to the frequency component of the motion-based signal. The parameter determining unit 440 may determine the filter parameter based on the determined parameter table. For example, the parameter determining unit 440 may set a reference value using the frequency component of the motion-based signal, and may determine a filter parameter corresponding to the reference value in the determined parameter table.

The parameter determining unit 440 may determine the filter parameter using a function relation between the frequency component of the motion-based signal and the filter parameter, rather than by selecting the filter parameter from the predetermined filter parameters. For example, the parameter determining unit 440 may set a reference value using the frequency component of the motion-based signal, and may derive the filter parameter by using the reference value as an input for the function relation, for example, a function relation defined by a formula.

The input signal filtering unit 450 may filter the input signal based on the filter parameter determined by the parameter determining unit 440. The input signal filtering unit 450 may apply the filter parameter determined by the parameter determining unit 440 to the filter, and may filter the input signal using the filter.

The filter used by the input signal filtering unit 450 may include, for example, an adaptive filter having a variable filter parameter. To determine an optimum filter coefficient of the adaptive filter, the parameter determining unit 440 may use an LMS algorithm, a least squares (LS) algorithm, or a recursive least squares (RLS) algorithm.

The input signal filtering unit 450 may filter the input signal using the motion-based signal and the filter adaptively. For example, when a filter used by the input signal filtering unit 450 is an adaptive filter, the input signal filtering unit 450 may filter the input signal using the motion-based signal as a reference signal. By filtering the input signal, the motion artifact may be removed from the input signal. An object signal that the user desires to output or measure, i.e., an artifact-free signal, may be outputted.

FIG. 5 is a flowchart illustrating an example of a signal processing method. Referring to FIG. 5, in 510, the signal processing apparatus may receive an input signal including a motion artifact. The signal processing apparatus may include, for example, a sensor attached to a body of a user to measure a biometric signal.

In 520, the signal processing apparatus may determine a filter parameter based on a frequency component of the motion-based signal analogous to the motion artifact.

The signal processing apparatus may determine the filter parameter for filtering the input signal based on the frequency component of the motion-based signal analogous to the motion artifact. The signal processing apparatus may determine the filter parameter based on the frequency component of the motion-based signal. For example, the signal processing apparatus may determine either one or both of a filter order and a filter coefficient based on the frequency component of the motion-based signal. The filter coefficient may include an adaptive constant of a filter.

The signal processing apparatus may convert the motion-based signal to a frequency domain, may identify a frequency band having a highest power based on a power per frequency band in the motion-based signal converted to the frequency domain, and may determine a filter parameter based on the identified frequency band. For example, the signal processing apparatus may identify the frequency band having the highest power based on the power per frequency band in the motion-based signal by performing an FFT on the motion-based signal.

The signal processing apparatus may select a filter parameter corresponding to the identified frequency band from predetermined filter parameters. For example, the signal processing apparatus may set a center frequency of the identified frequency band to be a reference value for determining a filter parameter, and may select a filter parameter corresponding to the reference value.

The signal processing apparatus may identify a frequency having a greatest magnitude by performing an FFT on the motion-based signal. The signal processing apparatus may set the frequency having the greatest magnitude to be a reference value for determining a filter parameter, and may select a filter parameter corresponding to the reference value.

The filter parameters corresponding to each reference value may be determined in advance, and may be stored, for example, in a lookup table. For example, the signal processing apparatus may identify a filter order or filter coefficient corresponding to the reference value in the lookup table, and may determine the identified parameter to be the filter parameter to be applied to the filter.

The signal processing apparatus may determine the filter parameter using a filter bank. For example, the signal processing apparatus may identify a frequency band having a highest mean value or a highest integral value based on a mean value or an integral value per frequency band in the motion-based signal, and may determine a filter parameter based on the identified frequency band. For example, the signal processing apparatus may select a filter parameter corresponding to the identified frequency band from predetermined filter parameters.

The signal processing apparatus may use the input signal in addition to the motion-based signal to determine the filter parameter to be applied to the filter. The signal processing apparatus may determine the filter parameter based on a relative frequency band difference between the frequency component of the input signal and the frequency component of the motion-based signal.

For example, the signal processing apparatus may set a first reference value using the frequency component of the input signal. The signal processing apparatus may convert the motion-based signal to a frequency domain, may identify a frequency band having a highest power based on a power per frequency band in the input signal converted to the frequency domain, and may set a center frequency of the identified frequency band to be a first reference value. The signal processing apparatus may identify a frequency band having a highest mean value or a highest integral value based on a mean value or an integral value per frequency band using a filter bank, and may set a center frequency of the identified frequency band to be a first reference value.

The signal processing apparatus may set a second reference value by performing the same method on the motion-based signal. The signal processing apparatus may determine whether the frequency band of the motion-based signal is higher or lower than the frequency band of the input signal by comparing the first reference value of the input signal to the second reference value of the motion-based signal. The signal processing apparatus may determine different parameters based on the determined result.

The signal processing apparatus may determine the filter parameter using a function relation between the frequency component of the motion-based signal and the filter parameter, rather than by selecting the filter parameter from the predetermined filter parameters. For example, the signal processing apparatus may set a reference value using the frequency component of the motion-based signal, and may derive the filter parameter by using the reference value as an input for the function relation.

In 530, the signal processing apparatus applies the filter parameter determined in 520 to the filter, and filters the input signal using the filter. For example, when the filter used by the signal processing apparatus is an adaptive filter, the signal processing apparatus may filter the input signal using the motion-based signal as a reference signal. By filtering the input signal, the motion artifact may be removed from the input signal. An object signal desired by the user to be measured or output, i.e., an artifact-free signal, may be outputted.

The signal processing apparatus 110 illustrated in FIG. 1 and the signal processing apparatus 410, the input signal receiving unit 420, the motion-based signal receiving unit 430, the parameter determining unit 440, and the input signal filtering unit 450 illustrated in FIG. 4 that perform the operations illustrated in FIGS. 2A-2D, 3A-3D, and 5 may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure may include specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A processor-implemented method of processing a signal, the method comprising:
    receiving at a sensor, by a receiving circuit, an input signal including a motion artifact;
    converting a motion-based signal analogous to the motion artifact to a frequency domain;
    identifying a frequency band having a highest power in the converted motion-based signal;
    determining a filter parameter based on the identified frequency band; and
    filtering the input signal using a filter based on the filter parameter,
    wherein the filter parameter is based on a relative frequency band difference between frequency components of the input signal and the motion-based signal,
    wherein the method further comprising:
    setting a first reference value corresponding to the input signal and a second reference value corresponding to the motion-based signal; and
    determining the filter parameter corresponding to each reference value in a pre-stored lookup table.

2. The processor-implemented method of claim 1, wherein the filter parameter corresponds to the identified frequency band.

3. The processor-implemented method of claim 1, wherein the filter parameter is further determined by identifying another frequency band having a highest mean value or a highest integral value based on a mean value or an integral value per frequency band in the motion-based signal using a filter bank.

4. The processor-implemented method of claim 3, wherein the filter parameter corresponds to the identified frequency band.

5. The processor-implemented method of claim 1, wherein the filter parameter is determined by a function relation between a frequency component of the motion-based signal.

6. The processor-implemented method of claim 1, wherein the filter parameter is based on at least one of an order of the filter or a coefficient of the filter based on a frequency component of the motion-based signal.

7. The processor-implemented method of claim 1, wherein the filter parameter is determined by:
    comparing a first reference value to the second reference value.

8. The processor-implemented method of claim 1, wherein the filter parameter is determined by identifying, in a lookup table, a filter order or a filter coefficient corresponding to a reference value.

9. A method of processing a signal, the method comprising:
    receiving at a sensor, by a receiving circuit, an input signal including a motion artifact;
    converting a motion-based signal analogous to the motion artifact to a frequency domain;
    identifying a frequency band having a highest power in the converted motion-based signal;
    determining a filter parameter based on the identified frequency band;
    applying the determined filter parameter to a filter to remove a motion artifact from the input signal,
    wherein the filter parameter is based on a relative frequency band difference between frequency components of the input signal and the motion-based signal,
    wherein the method is further comprising:
    setting a first reference value corresponding to the input signal and a second reference value corresponding to the motion-based signal; and
    determining the filter parameter corresponding to each reference value in a pre-stored lookup table.

10. An apparatus for processing a signal, wherein a processor comprises:
    an input signal receiving circuit configured to receive an input signal including a motion artifact;
    a parameter determining circuit configured to:
        convert the motion-based signal to a frequency domain;
        identify a frequency band having a highest power in the converted motion-based signal; and
        determine a filter parameter based on the identified frequency band; and
    an input signal filtering circuit configured to filter the input signal based on the filter parameter,
    wherein the parameter determining circuit is further configured to determine the filter parameter based on a relative frequency band difference between frequency components of the input signal and the motion-based signal,
    set a first reference value corresponding to the input signal and a second reference value corresponding to the motion-based signal; and
    determine the filter parameter corresponding to each reference value in a pre-stored lookup table.

11. The apparatus of claim 10, wherein the filter parameter corresponds to the identified frequency band.

12. The apparatus of claim 10, wherein the parameter determining circuit is further configured to determine the filter parameter based on identifying another frequency band having a highest mean value or a highest integral value based on a mean value or an integral value per frequency band in the motion-based signal using a filter bank.

13. The apparatus of claim 12, wherein the filter parameter corresponds to the identified frequency band.

14. The apparatus of claim 10, wherein the parameter determining circuit is further configured to determine the filter parameter using a function relation between the frequency component of the motion-based signal and the filter parameter.

15. The apparatus of claim 10, wherein the parameter determining circuit is further configured to determine either one or both of an order of the filter and a coefficient of the filter based on the frequency component of the motion-based signal.

16. The apparatus of claim 10, further comprising a motion-based signal receiving circuit configured to receive the motion-based signal analogous to the motion artifact.

* * * * *